United States Patent [19]
Prasad et al.

[11] Patent Number: 5,536,582
[45] Date of Patent: Jul. 16, 1996

[54] AQUEOUS SILICONE COATING COMPOSITIONS, METHOD OF COATING SUBSTRATES WITH THE SAME AND COATED SURGICAL NEEDLES PRODUCED THEREBY

[75] Inventors: Janniah S. Prasad; Dario Vitali, both of Fairfield, Conn.

[73] Assignee: American Cyanamid Company, Wayne, N.J.

[21] Appl. No.: 358,659

[22] Filed: Dec. 19, 1994

Related U.S. Application Data

[63] Continuation of Ser. No. 62,355, May 13, 1993, abandoned.

[51] Int. Cl.⁶ .............................. B32B 9/06; B32B 15/04
[52] U.S. Cl. ................ 428/450; 427/387; 427/388.4; 427/421; 427/600; 524/588; 524/862; 525/478; 528/31; 528/32; 606/222
[58] Field of Search ..................... 427/228, 387, 427/388.4, 421, 600; 428/450; 524/588, 862; 525/478; 528/31, 32; 606/222

[56] References Cited

U.S. PATENT DOCUMENTS

| | | | |
|---|---|---|---|
| 3,574,673 | 4/1971 | Schweiger | 428/450 X |
| 4,509,981 | 4/1985 | Sanders, Jr. et al. | 106/3 |
| 4,534,363 | 8/1985 | Gold | 128/772 |
| 4,720,521 | 1/1988 | Speilvogel et al. | 524/862 |
| 4,791,029 | 12/1988 | Fai et al. | 427/387 X |
| 4,806,430 | 2/1989 | Spielvogel et al. | 428/450 |
| 4,844,986 | 7/1989 | Karakelle et al. | 427/387 X |
| 4,905,695 | 3/1990 | Bendel et al. | 606/222 |
| 4,959,068 | 9/1990 | Bendel et al. | 606/222 |
| 5,258,013 | 11/1993 | Granger et al. | 606/223 |

FOREIGN PATENT DOCUMENTS

| | | |
|---|---|---|
| 0494648 | 7/1992 | European Pat. Off. . |
| 0500229 | 8/1992 | European Pat. Off. . |

OTHER PUBLICATIONS

Abstract of JP 3080869 (Apr. 5, 1991).

*Primary Examiner*—Michael Lusignan
*Attorney, Agent, or Firm*—Montgomery W. Smith; Charles F. Costello, Jr.; Rita D. Vacca

[57] ABSTRACT

An aqueous silicone coating composition containing a reactive siloxane polymer and a non-reactive dimethylpolysiloxane in an aqueous carrier having an effective amount of at least one dispersing agent to disperse the siloxanes throughout the aqueous carrier. Also provided is a method of lubricating substrates by applying an aqueous silicone coating composition to the substrate and curing the silicone thereon, as well as lubricated surgical needles prepared by that method.

30 Claims, No Drawings

AQUEOUS SILICONE COATING COMPOSITIONS, METHOD OF COATING SUBSTRATES WITH THE SAME AND COATED SURGICAL NEEDLES PRODUCED THEREBY

This application is a continuation of application Ser. No. 08/062,355 filed May 13, 1993, abandoned.

BACKGROUND OF THE INVENTION

1. Field of the Invention

This invention is directed to an aqueous silicone coating composition for providing lubricity to substrates, such as suture needles, hypodermic needles or razor blades. The invention is also directed to a method of coating such substrates with an aqueous silicone composition and the coated surgical needles produced thereby.

2. Related Background Art

Silicone compositions have been used to coat, and thus provide lubricity to, various articles of manufacture. U.S. Pat/ No. 3,574,673 describes coating articles having fine cutting edges with copolymers of methylsiloxane and aminoalkylsiloxane. This reference discloses applying the copolymer through the use of an inert solvent carrier, such as isopropyl alcohol, toluene or benzene.

U.S. Pat. Nos. 4,720,521 and 4,806,430 disclose the use of a film-forming composition, comprising three different reactive siloxane polymers and a non-reactive lubricating siloxane polymer, that is applied and used on a substrate, such as a hypodermic needle, to increase the lubricity of that substrate. The film-forming siloxane compositions of these references are applied to the desired substrate by using an inert, organic solvent carrier, such as a chlorofluorocarbon (e.g., those materials known by the trademark Freon®.)

European Patent Application Publication No. 494,648 describes a coated surgical needle prepared by applying to a surgical needle a curable silicone composition comprising an aminoalkyl siloxane and at least one other copolymerizable siloxane. A mixture of dimethyl cyclosiloxane and dimethoxysilyldimethylamino-ethylaminopropyl silicone polymer is disclosed as the preferred silicone composition. This reference teaches that the silicone composition is applied to the surgical needle as a solution in an organic solvent such as hexane, trichlorotrifluoroethane, 1,1,1-trichloroethane or mineral spirits.

European Patent Application Publication No. 500,229 discloses a method of coating a suture needle by depositing a silicone solution containing a silicone and a solvent on the needle. The solution-coated needle is subsequently exposed to a gas atmosphere to form a layer of silicon adjacent and adhered to the outer surface of the needle. The remaining unadhered silicon is removed from the needle with a solvent. The reference teaches polydimethylsiloxane as an exemplary silicone, while acetone, a Freon® chlorofluorocarbon, trichloroethane or methylene chloride are mentioned as exemplary solvents.

Prior to this time, silicon coating solutions used to impart lubricity to various articles of manufacture, such as suture needles and razor blades, have required the presence of an inert organic solvent carrier. However, organic fluorocarbon solvents employed in many of these compositions are known to be detrimental to the atmospheric ozone layer and their use is being phased out by worldwide treaty. Additionally, other organic solvents used in known coasting compositions are either toxic or environmentally hazardous. The organic solvents used in known silicone coating compositions also increase the costs of those compositions, particularly since they are a large percentage of the compositions.

It is an object of this invention to provide a novel aqueous silicone coating composition which can be used to effectively lubricate substrates, such as suture needles, without the substantial use of organic solvent carriers.

It is a further object of this invention to provide a method for lubricating a substrate by applying an aqueous silicone coating composition to the substrate and thereafter curing the silicone thereon.

It is also an object of this invention to provide a suture needle having excellent lubricating properties prepared by the process of coating the needle with an aqueous silicone coating composition and curing the silicone thereon.

SUMMARY OF THE INVENTION

This invention relates to a silicone coating composition comprising an aqueous mixture comprised of a non-reactive polydimethylsiloxane, a reactive siloxane polymer, and an effective amount of at least one dispersing agent to disperse the siloxanes throughout the aqueous solution. Although it is well known that siloxanes are not readily soluble in water, the inventors have discovered that a mixture of siloxanes finely dispersed in a water carrier through the use of dispersing agents provides an aqueous based silicone coating composition that is an effective lubricating composition. Significantly, the aqueous silicone coating composition of this invention is substantially free of organic solvent carrier. By substantially free, it is meant that the predominant carrier is water. However, small amounts of organic solvents, i.e., up to about 15 percent of the total weight of the composition, are permissible. Preferably, the maximum amount of organic solvent is 10 percent of the total weight of the composition.

It is preferable that the reactive siloxane polymer of the aqueous silicone coating composition is a mixture of an aminoalkyl siloxane and at least one other copolymerizable siloxane, such as a polyalkylsiloxane or a cyclosiloxane. The aqueous silicone coating composition of this invention most preferably contains a cyclosiloxane. Furthermore, the preferred coating composition of this invention will contain a mixture of polyethylene glycol and octylphenoxy polyethoxyethanol as dispersing agents.

This invention is further directed to an aqueous silicone coating composition consisting essentially of an aminoalkyl siloxane, a dimethyl cyclosiloxane, a non-reactive polydimethylsiloxane, a polyethylene glycol, an octylphenoxy polyethoxyethanol and an aqueous carrier, wherein the polyethylene glycol and octylphenoxy polyethoxyethanol are present in the composition in an amount effective to disperse the siloxanes throughout the aqueous carrier.

Another aspect of this invention relates to a method of lubricating a substrate by applying an aqueous silicone coating composition to the surface of the substrate and curing the silicone thereon. The aqueous silicone coating composition that can be employed in the lubricating method of this invention must have at least one siloxane polymer and an effective amount of at least one dispersing agent to essentially disperse the siloxane throughout the aqueous carrier of the composition. The siloxane polymer can be a polymerizable siloxane, such as an aminoalkyl siloxane or a dimethyl cyclosiloxane, or a non-reactive siloxane, such as a polydimethylsiloxane. Preferably, a mixture of polymerizable siloxanes are employed in the aqueous silicone coating composition used in this method. A mixture of polymerizable siloxanes and a non-reactive siloxane is most preferred. The composition can be applied by methods, such as spraying, dipping, wicking, or by ultrasonic atomizing methods. A composition thus applied to the surface of the substrate may be cured using conventional cure techniques that cause at least some polymerization of the reactive siloxanes present in the composition and adherence of the resulting silicone polymer to the surface of the substrate.

A further aspect of this invention is directed to a lubricated surgical needle produced by applying an aqueous silicone coating composition to a surgical needle and curing the silicone on the surgical needle. Surgical needles lubricated with an aqueous silicone coating composition that is substantially free of organic solvent carrier show excellent lubricating properties. The penetration and drag performance of surgical needles coated with the aqueous silicone composition of this invention were comparable to those coated by conventional methods, i.e., with organic solvent carriers. Moreover, the treated surgical needles exhibited particularly improved performance over that of uncoated needles or Commercially available silicone coated needles (FS-2 Ethicon Inc.).

DETAILED DESCRIPTION OF THE INVENTION

The aqueous silicone coating composition of the present invention is an aqueous mixture comprised of a non-reactive polydimethylsiloxane, a reactive siloxane polymer and at least one dispersing agent. The preferred reactive siloxane polymer of the composition of this invention is a mixture of at least two copolymerizable siloxanes, such as an polyalkylsiloxane or, most preferably, a cyclosiloxane in combination with an aminoalkyl siloxane. The total amount of siloxanes present is from about 0.5 to 20 percent by weight, based on the weight of the total composition (hereinafter, "%w/w"). Unless indicated otherwise, all weight percentages stated herein are based on the total weight of the aqueous compositions. More particularly, usually from about 0.1 to 2.0 %w/w of non-reactive polydimethylsiloxane and from about 0.5 to 10.0 %w/w of aminoalkyl siloxane are employed in the composition. When an additional copolymerizable siloxane, such as cyclosiloxane, is used, it is preferably present in an amount from about 0.5 to 7.0 %w/w,. Generally, it is desirable to adjust the total amount of silicone present in the composition to provide a degree of lubricity required for the particular application in which the composition will be used, while using the least amount of silicone possible..

A suitable mixture of aminoalkyl siloxane and polyalkylsiloxane which can be employed in the composition of this invention is described in U.S. Pat. No. 3,574,673, the contents of which are incorporated by reference herein. That mixture includes (a) from about 5–20 weight percent of an aminoalkyl siloxane of the formula

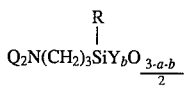  I in which R is a lower alkyl radical containing no more than 6 carbon atoms; Y is selected from the group consisting of —OH and —OR' radicals in which R' is an alkyl radical of no more than 3 carbon atoms; Q is selected from the group consisting of hydrogen, —CH$_3$, and —CH$_2$CH$_2$NH$_2$; a has a value of 0 or 1, and b has a value of 0 or 1 and the sum of a+b has a value of 0, 1 or 2, and (b) from about 80 to 95.weight percent of a methyl substituted siloxane of the formula

  II in which R" is selected from the group consisting of —OH and —CH$_3$ radicals and c has a value of 1 or 2.

Preferably, one or more cyclosiloxanes can be substituted for the methyl substituted siloxane (b) of the above described mixture. Examples of the cyclosiloxanes which may be employed in the present composition are described in the "Encyclopedia of Polymer Science and Engineering", Mark et al., eds., 2nd ed., John Wiley & Sons (1989), Vol. 15, p.207 et seq., the contents of which are incorporated by reference herein.

A particularly preferred source of aminoalkyl siloxane and an additional copolymerizable siloxane, namely cyclosiloxane, employed in the present invention is MDX-4-4159 Fluid ("MDX Fluid") (trade name of Dow Corning Corporation). MDX Fluid is a 50 percent active solution of dimethyl cyclosiloxane and dimethoxysilyldimethylaminoethylaminopropyl silicone polymer in a mixture of stoddard solvent (mineral spirits) and isopropyl alcohol. The amount of MDX Fluid employed in the coating composition of this invention is preferably an amount in the range of about 1.0 to 20 %w/w. 365 Medical-Grade Emulsion (a tradename of Dow Corning), which is an emulsion of 360 Medical Fluid (a tradename of Dow Corning)(360 Medical Fluid consists of non-reactive polydimethylsiloxane), is a particularly preferred source of the non-reactive polydimethylsiloxane employed in the present coating composition. Specifically, 365 Medical-Grade Emulsion contains approximately 35% polydimethylsiloxane, 1% propylene glycol, 2% octylphenoxy polyethoxyethanol and 1% sorbitan monolaurate in water. The 365 Medical-Grade Emulsion is preferably present in the aqueous silicone coating composition in an amount in the range of about 0.5 to 15 %w/w.

The dispersing agent(s) required in the coating compositions of this invention essentially disperse the siloxanes throughout the aqueous mixture or carrier. Any dispersing agent, including emulsifying agents, that promotes the essentially uniform dispersion of siloxanes throughout the aqueous mixture in the form of a suspension may be employed in the aqueous composition of this invention. Any of the general types of anionic, cationic or nonionic emulsifying agents may be employed as a dispersing agent in this invention. They include anionic surfactants, such as salts of fatty acids or alkane sulfonic acids and nonionics based on polyether groupings, sugar derivatives or propylene glycol. The dispersing agent or mixture of dispersing agents must be used in an amount effective to obtain a homogeneous dispersion of the siloxanes in the aqueous mixture.

Preferably, the dispersing agent is a mixture of propylene glycol and an octylphenoxy polyethoxyethanol, such as IGEPAL®CO-630, a trademark of GAF. The octylphenoxy polyethoxyethanol dispersing agent is represented by the formula:

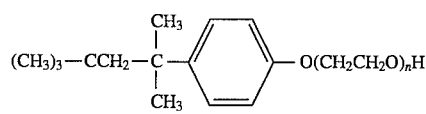

wherein n is in the range of about 5 to 15. The most preferred dispersing agent, IGEPAL® CO-630, is octylphenoxy polyethoxyethanol wherein n is 9 to 10.

Most preferably, propylene glycol is present in an amount ranging from 0.5 to 2.0 %w/w and IGEPAL® CO -630 is present in an amount ranging from 0.5 to 2.0 %w/w.

The coating composition is prepared by dispersing the siloxanes and dispersing agents in an aqueous carrier. Preferably the aqueous carrier will be from about 65 to 97 percent by weight of the total composition. The composition can be prepared by mixing the ingredients in any manner that will result in a homogeneous dispersion of the siloxanes in the aqueous carrier. It is preferred, however, to mix the dispersants with the siloxanes and then dilute the siloxane/dispersant mixture with deioninized water to obtain the aqueous silicone coating composition. The pH of the coating composition can be adjusted as required by the addition of any acid or base that does not interfere with the dispersion or ultimate polymerization of the siloxanes.

The method of this invention for lubricating a substrate comprises applying an aqueous silicone coating composition to the substrate and curing the silicone thereon. Any aqueous silicone composition having at least one siloxane polymer and at least one dispersing agent present in an effective amount to disperse the siloxane throughout the aqueous carrier can be employed in the present method. The siloxane present in the aqueous compositions employed in this method can be a reactive polymerizable siloxane or a non-reactive siloxane. Preferably the aqueous composition will contain a mixture of polymerizable siloxanes like those found in MDXL Fluid. On the other hand, the aqueous composition may contain only a non-reactive siloxane, such as the non-reactive polydimethylsiloxane contained in 365 Medical-Grade Emulsion. However, the most preferred aqueous silicone composition employed in the lubricating method of this invention is the novel aqueous silicone coating composition described above.

The aqueous silicone coating composition may be applied to a substrate, for example, by either spraying, dipping, wicking or by ultrasonic atomization. Any type of application which sufficiently coats the substrate being treated with the aqueous silicone composition may be employed in this method.

The amount of silicone polymer ultimately present on a treated substrate can be controlled by varying the time over which the aqueous silicone coating composition is applied to the substrate. For example, if the aqueous composition is applied by ultrasonic atomization, then the lubricity of the substrate can be increased by making multiple passes of the substrate through the atomized environment. Similarly, increased lubricity can be achieved by lengthening the application time during spraying or the exposure time when dipping. The application time will vary depending on the type of application employed and the degree of lubricity required for the treated substrate. Generally, the more lubricity required the heavier the coating.

Curing of the reactive siloxanes employed in the coating composition is achieved by conventional methods well known in the art. For example, heat curing in an oven or by application of radio frequency are useful cure methods. Any cure method which causes at least some polymerization of the reactive siloxanes in the coating composition is applicable. When oven curing, it is preferable to heat the coated substrate at a temperature in the range from about 80° to 200° C. and for a time in the range of about 0.5 to 6 hours, depending upon the precise formulation of the composition. The temperature and time of curing are optimized to achieve polymerization of the reactive siloxanes present in the composition, adherence of the polymerized silicone to the substrate and removal of the aqueous carrier.

The method of lubricating can be used on any substrate, such as metal or plastic, which requires a dry lubricant. It has been found to be particularly useful for lubricating surgical needles, especially when applied by spraying or atomization since these methods of application have been found to improve suture holding strength over methods such as dipping. Surgical needles lubricated by the method of this invention exhibited a similar degree of lubricity in multiple pass application in an animal tissue when compared to prior art coating techniques employing siloxanes in organic solvent carriers.

This invention is also directed to a lubricated surgical needle prepared by the process of applying an aqueous silicone coating composition to the surgical needle and curing the silicone thereon. Preferably, the lubricated surgical needles are prepared using the novel aqueous silicone coating composition described above, i.e., an aqueous solution comprised of a non-reactive polydimethylsiloxane, a reactive siloxane polymer, and an effective amount of at least one dispersing agent to disperse the Siloxanes throughout the aqueous solution. Most preferably, the novel aqueous silicone coating composition is applied by spraying or atomization so that the resulting lubricated suture needle exhibits enhanced suture holding strength. The lubricated surgical needles of this invention exhibit penetration and drag performance comparable to prior art needles lubricated with silicones in organic solvent carrier and superior to uncoated needles and commercially available silicone coated needles (FS-2 Ethicon Inc.).

As described above, the lubricity of the surgical needles of this invention can be increased by varying the degree of application of the aqueous silicone coating composition or by varying the silicone concentration of the coating composition. For example, it is preferable to prepare lubricated cardiovascular surgical needles with an aqueous silicone coating composition containing a total amount of silicone in a range from about 1.0 to 1.5 %w/w. On the other hand, larger surgical needles are preferably coated with an aqueous silicone coating composition containing a total amount of silicone in a range of from about 10 to 15 %w/w.

The examples which follow are intended as an illustration of certain preferred embodiments of the invention, and no limitation of the invention is implied. In the following examples, all amounts are in percent by weight of the total composition.

EXAMPLE I

The following aqueous silicone composition was prepared:

| Composition | Amount (Parts by weight) |
| --- | --- |
| 365 Medical-Grade Emulsion[+] | 2.41 |
| MDX 4-4159 Fluid[++] | 10.84 |
| Propylene glycol | 1.20 |
| IGEPAL CO-630 | 1.20 |
| water | 84.35 |
|  | 100.00 |

[+]365 Medical-Grade Emulsion - 35% polydimethylsiloxane, 1% propylene glycol, 2% octylphenoxy polyethoxyethanol and 1% sorbitan monolaurate in water.
[++]MDX 4-4159 Fluid - 50% dimethyl cyclosiloxane and dimethoxysilyldimethylaminoethylaminopropyl silcone polymer in a mixture of stoddard solvent (mineral spirits) and isopropyl alcohol.

Propylene glycol (2 gm) and IGEPAL CO-630 (2 gm) were added to MDX 4-4159 fluid (18 gm). To this mixture was added 365 Medical-Grade Emulsion (4 gm), followed by the addition of water (140 gm) with stirring to form a homogeneous emulsion. This aqueous silicone coating composition contained approximately 6.3% by weight of silicone.

COMPARATIVE EXAMPLE II

A non-aqueous silicone coating composition was prepared by dissolving 360 Medical Fluid and MDX 4-4159 fluid in Freon TR®, which is trichlorotrifluoroethane. The resulting organic carrier based coating composition contained 7.5% silicone.

EXAMPLE III

The aqueous silicone coating composition prepared in Example I (Solution #1) was applied to a group of T-12 needles (Sulzle Inc.) by spraying in a coating booth. The 7.5% silicone-Freon® solution of Comparative Example II (Solution #2) was applied similarly to a second set of T-12 needles. Both groups of needles were simultaneously cured in an oven at about 125° C. for approximately two hours. The needles were evaluated for penetration and drag performance, the results of which are summarized in Table 1 below. These results show that needles lubricated with the aqueous silicone coating composition of this invention were superior in drag performance and nearly as efficient in penetration force when compared to needles coated with a coating composition containing an organic solvent carrier.

TABLE 1

COATING EVALUATION
T-12 NEEDLES

| NEEDLE | SOLUTION | DRAG FORCE, GRAMS | | | DRAG RATIO | PENETRATION FORCE, GRAMS | | |
|---|---|---|---|---|---|---|---|---|
| | | AVG. | S.D. | RANGE | | AVG. | S.D. | RANGE |
| T-12 | #2 | 90.0 | 10.0 | 68–112 | 1.30 | 152.8 | 17.5 | 120–172 |
| T-12 | #1 | 83.7 | 6.4 | 68–96 | 1.26 | 145.3 | 15.2 | 120–172 |

DRAG FORCE AVERAGES BASED ON FIVE NEEDLES, TEN PENETRATIONS PER NEEDLE IN 2.4 MM RUBBER. PENETRATION FORCE AVERAGES BASED ON FIVE NEEDLES, THREE PENETRATIONS PER NEEDLE IN 2.4 MM RUBBER.
ALL NEEDLES UNATTACHED AND UNSTERILIZED.
S.D. - Standard deviation

EXAMPLE IV

Unattached CE-4 needles (Sulzle Inc., lot #145885), were divided into four groups. The first group was coated with the silicone-Freon® Solution #2 of Comparative Example II. The second group was coated by passing it once under a stream of ultrasonically atomized Solution #1 of Example I. The third group was exposed twice to the atomized Solution #1. Ultrasonic atomization of the aqueous composition was achieved through the use of an ultrasonic atomizing device of Sonic and Materials Company, Danbury, Connecticut. A fourth group of needles was left uncoated. The coated needles were all cured at about 125° C. for approximately two hours. The three groups of coated needles, the group of uncoated needles and a group of commercially available needles, (Ethicon Inc. FS-2, lot #Zk9404) were subject to penetration and drag force testing. The results of these tests are summarized in Tables 2 and 3 below.

TABLE 2

SHARPNESS EVALUATION

| NEEDLE | COATING SOLUTION/ CONDITIONS | PENETRATION FORCE, GRAMS | | |
|---|---|---|---|---|
| | | AVG. | S.D. | RANGE |
| CE-4 | #2 | 180.0 | 26.5 | 90–220 |
| CE-4 | UNCOATED | 261.0 | 48.3 | 170–340 |
| CE-4 | #1/ONE PASS | 194.3 | 56.4 | 140–390 |
| CE-4 | #1/TWO PASSES | 173.0 | 34.7 | 110–250 |
| FS-2 | — | 399.0 | 120.3 | 180–590 |

AVERAGES BASED ON 10 NEEDLES, 3 PENETRATIONS PER NEEDLE IN THICK RABBIT SKIN.

TABLE 2-continued

SHARPNESS EVALUATION

| NEEDLE | COATING SOLUTION/ CONDITIONS | PENETRATION FORCE, GRAMS | | |
|---|---|---|---|---|
| | | AVG. | S.D. | RANGE |

ALL NEEDLES UNATTACHED EXCEPT F5-2 NEEDLE.
S.D. - Standard deviation

| | DRAG EVALUATION | | | | |
|---|---|---|---|---|---|
| NEEDLE | COATING SOLUTION/ CONDITIONS | DRAG FORCE, GRAMS | | | DRAG RATIO |
| | | AVG. | S.D. | RANGE | |
| CE-4 | #2 | 64.4 | 16.3 | 40–120 | 1.91 |
| CE-4 | UNCOATED | 392.2 | 118.2 | 120–594 | 1.04 |
| CE-4 | #1/ONE PASS | 157.4 | 69.8 | 40–340 | 3.76 |
| CE-4 | #1/TWO PASSES | 112.0 | 37.0 | 40–180 | 3.15 |
| FS-2 | — | 192.3 | 162.3 | 30–620 | 5.57 |

AVERAGES BASED ON 5 NEEDLES, 10 PENETRATIONS PER NEEDLE IN 2.4 MM RUBBER.
ALL NEEDLES UNATTACHED EXCEPT FS-2 NEEDLE.
S.D. - Standard deviation The data shows that needles coated with an aqueous silicone coating composition have superior penetration and drag performance compared to uncoated needles or Ethicon needles. The data also shows that the needles coated with the aqueous silicone coating composition of this invention were equivalent in penetration force but not as efficient in drag performance as the needles coated with the silicone-Freon® composition. However, the data also indicate that multiple passes of the needle through the atomized aqueous silicone coating composition increased the lubricity of those needles. Scanning electron microscopy (SEM) was conducted on a needle selected from each of the coated needles and an uncoated needle. The SEM analysis showed that the surface of the needle coated with the Freon®-silicone composition contained the greatest amount of silicone. The needle coated twice with the aqueous silicone coating composition had a lesser, but detectable amount of silicone. On the other hand, the needle only coated once with the aqueous composition was practically indistinguishable from the uncoated needle by SEM. The SEM data appears to indicate that only a very small amount of silicone is necessary to improve the penetration characteristics of a needle, while a greater amount is required to improve drag performance.

EXAMPLE V

The following aqueous silicone composition can be prepared:

| Composition | Amount (Parts by weight) |
|---|---|
| 365 Medical-Grade Emulsion | 3.56 |
| MDX 4-4159 Fluid | 12.50 |
| Propylene glycol | 1.25 |
| IGEPAL CO-360 | 1.25 |
| Deionized Water | 81.44 |
| | 100.00 |

The MDX 4-4159 fluid (20.0 gm) is mixed with propylene glycol (2.0 gm) and IGEPAL CO -630(2.0 gm). To this mixture is added 365 Medical-Grade Emulsion (5.7 gm). The siloxane/emulsifier mixture is then combined with deionized water (130.3 gm) and mixed with a magnetic stirrer until a fine emulsion of siloxanes in the aqueous carrier is obtained. This aqueous silicone coating composition contains 7.5%by weight of silicone.

Other variations and modifications of this invention will be obvious to those skilled in this art. This invention is not to be limited except as set forth in the following claims.

We claim:

1. A silicone coating composition consisting essentially of an aqueous mixture of a non-reactive polydimethylsiloxane, a reactive siloxane polymer and an effective amount of at least one dispersing agent to disperse said siloxanes throughout the aqueous mixture, wherein the reactive siloxane polymer is a mixture of an aminoalkyl siloxane and a copolymerizable siloxane selected from the group consisting of a polyalkylsiloxane, a cyclosiloxane and mixtures thereof, and wherein the aqueous mixture contains said siloxanes in an amount of at least about 0.5 percent by weight of the total composition and water in an amount of at least about 65 percent by weight of the total composition.

2. The coating composition of claim 1, wherein the copolymerizable siloxane is a cyclosiloxane.

3. The coating composition of claim 2 wherein the dispersing agent is selected from the group consisting of propylene glycol, an octylphenoxy polyethoxyethanol of the formula:

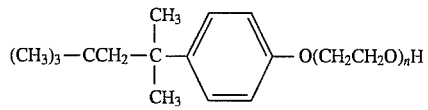

wherein n is in a range of about 5 to 15 and a mixture thereof.

4. The coating composition of claim 3, wherein the silicone in the silicone coating composition is in a range of from about 0.5 to 20 percent by weight of the composition.

5. The coating composition of claim 4, wherein the aqueous mixture contains an amount of water in the range of about 65 to about 97 weight percent of the total composition.

6. The coating composition of claim 3, wherein the propylene glycol is an amount in the range from about 0.5 to 2.0 %w/w and the octylphenoxy polyethoxyethanol is an amount in the range from about 0.5 to 2.0 %w/w.

7. An aqueous silicone coating composition consisting essentially of about 0.5 to 10.0 percent by weight of the total composition of an aminoalkyl siloxane, about 0.5 to 7.0 percent by weight of the total composition of a dimethyl cyclosiloxane, about 0.1 to 2.0 percent by weight of the total composition of a non-reactive dimethylpolysiloxane, a polyethylene glycol, an octylphenoxy polyethoxyethanol and an aqueous carrier, wherein the polyethylene glycol and octylphenoxy polyethoxyethanol are present in the composition in an amount effective to disperse said siloxanes throughout the aqueous carrier, and wherein the aqueous carrier contains an amount of water in the range of about 65 to 97 percent by Weight of the total composition.

8. A method for lubricating a substrate with silicone comprising applying an aqueous silicone coating composition to the surface of the substrate and curing the silicone thereon, wherein the aqueous silicone coating composition is an aqueous mixture of at least about 0.5 percent by weight of the total composition of a silicone polymer and an amount of at least one dispersing agent effective to disperse said siloxane throughout the aqueous mixture, wherein the silicone polymer is a non-reactive polydimethylsiloxane or a reactive siloxane polymer selected from the group consisting of an aminoalkyl siloxane, a polyalkylsiloxane, a cyclosiloxane and mixtures thereof, and wherein the aqueous mixture contains water in an amount of at least about 65 percent by weight of the total composition.

9. The method of claim 8 wherein said siloxane polymer is the non-reactive polydimethylsiloxane.

10. The method of claim 8 wherein said siloxane polymer is the reactive siloxane polymer.

11. The method of claim 10 wherein the reactive siloxane polymer is a mixture of at least two copolymerizable siloxanes.

12. The method of claim 11 wherein said mixture of copolymerizable siloxanes comprises cyclosiloxane and aminoalkyl siloxane.

13. The method of claim 12 wherein said siloxane polymer further comprises a non-reactive polydimethylsiloxane polymer.

14. The method of claim 13 wherein the dispersing agent is selected from the group consisting of propylene glycol, an octylphenoxy polyethoxyethanol of the formula:

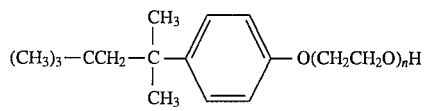

wherein n is in the range of about 5 to 15 and a mixture thereof.

15. The method of claim 14 wherein the curing step is performed at a temperature in the range of about 80 to 200° C. for a time of about 0.5 to 6 hours.

16. The method of claim 8.wherein the substrate is a surgical needle.

17. The method of claim 16 wherein the aqueous silicone coating composition is applied by spraying or ultrasonic atomization.

18. The method of claim 8, wherein the silicone in the aqueous silicone composition is in a range of from about 0.5 to 20 percent by weight of the composition.

19. A lubricated surgical needle prepared by the process of lubricating a needle with a silicone comprising applying an aqueous silicone coating composition to the surface of the needle and curing the silicone thereon, wherein the aqueous silicone coating composition is an aqueous mixture of a siloxane polymer and an amount of at least one dispersing agent effective to disperse said siloxane throughout the aqueous mixture.

20. The lubricated surgical needle of claim 19 wherein said siloxane polymer is a non-reactive polydimethylsiloxane.

21. The lubricated surgical needle of claim 19 wherein said siloxane polymer is a reactive siloxane polymer.

22. The lubricated surgical needle of claim 21 wherein the reactive siloxane polymer is a mixture of at least two copolymerizable siloxanes.

23. The lubricated surgical needle of claim 22 wherein said mixture of copolymerizable siloxanes comprises a cyclosiloxane and an aminoalkyl siloxane.

24. The lubricated surgical needle of claim 23, wherein said siloxane polymer further comprises a nonreactive polydimethylsiloxane polymer.

25. The lubricated surgical needle of claim 24 wherein the dispersing agent is selected from the group consisting of propylene glycol, an octylphenoxy polyethoxyethanol of the formula:

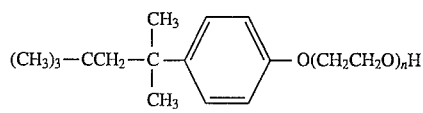

wherein n is in the range of about 5 to 15 and a mixture thereof.

26. The lubricated surgical needle of claim 25 wherein the curing step is performed at a temperature in the range of about 80° to 200° C. for a time of about 0.5 to 6 hours.

27. The lubricated surgical needle of claim 26 wherein the aqueous silicone coating composition is applied by spraying or ultrasonic atomization.

28. The lubricated surgical needle of claim 19, wherein the silicone in the aqueous silicone composition is in a range of from about 0.5 to 20 percent by weight of the composition.

29. A lubricated surgical needle prepared by the process of lubricating a needle with silicone comprising applying an aqueous silicone coating composition to the surface of the needle and curing the silicone thereon, wherein the aqueous silicone coating composition is an aqueous mixture of a silicone polymer and an amount of at least one dispersing agent effective to disperse said siloxane throughout the aqueous mixture, wherein the silicone polymer is a non-reactive polydimethylsiloxane or a reactive siloxane polymer selected from the group consisting of an aminoalkyl siloxane, a polyalkylsiloxane, a cyclosiloxane and mixtures thereof.

30. A lubricated surgical needle prepared by the process of lubricating a needle with silicone comprising applying an aqueous silicone coating composition to the surface of the needle and curing the silicone thereon, wherein the aqueous silicone coating composition is an aqueous mixture of at least about 0.5 percent by weight of the total composition of a silicone polymer and an amount of at least one dispersing agent effective to disperse said siloxane throughout the aqueous mixture, wherein the silicone polymer is a non-reactive polydimethylsiloxane or a reactive siloxane polymer selected from the group consisting of an aminoalkyl siloxane, a polyalkylsiloxane, a cyclosiloxane and mixtures thereof, and wherein the aqueous mixture contains water in an amount of at least about 65 percent by weight of the total composition.

* * * * *

UNITED STATES PATENT AND TRADEMARK OFFICE
CERTIFICATE OF CORRECTION

PATENT NO. : 5,536,582

DATED : July 16, 1996

INVENTOR(S) : Janniah S. Prasad; Dario Vitali

It is certified that error appears in the above-identified patent and that said Letters Patent are hereby corrected as shown below:

In Column 5, line 24, delete "MDXL" and insert -- MDX --.

In Column 8, line 46, delete "F5-2" and insert -- FS-2 --.

In Column 8, line 52, insert -- Table 3 --.

Signed and Sealed this

Twentieth Day of May, 1997

Attest:

BRUCE LEHMAN

Attesting Officer           Commissioner of Patents and Trademarks